US005766607A

United States Patent [19]

Fenwick et al.

[11] Patent Number: 5,766,607

[45] Date of Patent: Jun. 16, 1998

[54] **METHOD OF CULTURING *M. BOVIS* IN LOW AVAILABLE IRON MEDIA AND ISOLATION OF OUTER MEMBRANE PROTEINS**

[75] Inventors: Bradley W. Fenwick, Manhattan; Maureen A. Rider, Westmoreland; Alan H. Brightman, II, Manhattan, all of Kans.

[73] Assignee: Kansas State University Research Foundation, Manhattan, Kans.

[21] Appl. No.: 546,902

[22] Filed: Oct. 23, 1995

Related U.S. Application Data

[63] Continuation of Ser. No. 328,865, Oct. 25, 1994, abandoned.

[51] Int. Cl.$^6$ .................... A61K 39/02; A61K 39/095; C12P 21/02; C12N 5/02

[52] U.S. Cl. .................... 424/251.1; 424/184.1; 424/234.1; 424/266.1; 435/69.3; 435/70.1; 435/7.32; 435/240.47

[58] Field of Search .................... 424/184.1, 234.1, 424/251.1, 266.1; 435/69.3, 70.1, 7.32, 240.47

[56] References Cited

U.S. PATENT DOCUMENTS

| | | |
|---|---|---|
| 4,675,176 | 6/1987 | Gerber . |
| 5,225,194 | 7/1993 | Suer . |

OTHER PUBLICATIONS

Billson et al FEMS Microbiol Letters 124:69–74, 1994.
Troutt et al Norden News, Summer 1985 pp. 28–35, 1985.
Gatewood et al, Vet. Microbiol, 41:221–233, 1994.
Niven et al, Mol. Microbiol 3(8):1083–1089, 1989.
Snipes et al Am. J. Vet. Res. 49(8): 336–, 1988.
Deneer et al J. Gen. Microbiol 135: 435–43, 1989.
Davies et al J. Gen. Microbiol, 138: 909–922, 1992.
Chart et al. J. Gen. Microbiol 132: 1373–78, 1986.
Kagonyera et al, Am J. Vet. Res. 50(1): 18–21, 1989.
Confer et al, Am. J. Vet. Res. 53(5): 646–52, 1992.
Confer et al Am. J. Vet. Res. 53(4):472–476, 1992.
Poolman Novel Strategies in Design & Production of Vaccines, ed. Cohen et al. pp. 73–77, 1996.
Chen et al, Infection & Immunity, 64(6):1900–1905, Jun. 1996.
Wetzler et al, J. Infectious Disease, 166:551–555, 1992.
Campos et al, Invest. Ophthalmol. & Vis. Sci. 36(8):1477–1491, Jul. 1995.
Current Protocols in Molecular Biology; Section II, pp. 10.2.1–10.2.5, John Wiley & Sons, 1987.
McMichael, Bacterial Differentiation Within *Moraxella Bovis*Colonies Growing at the Interface of the Agar Medium with the Petri Dish, Journal of General Microbiology (1992), 138, 2687–2695.
Riley, Growth Requirements for *Moraxella Bovis*, Veterinary Microbiology, 9 (1984) 593–598.
Ostle et al., Outer Membrane Protein Antigens of *Moraxella Bovis*, Am. J. Vet. Res., vol. 47, No. 7, Jul., 1986.
Smith, et al.; Effectiaveness of Two Commercial Infectious Bovine Keratoconjunctivitis Vaccines; Am. J. Vet. Res., vol. 51, No. 7, Jul. 1990.

*Primary Examiner*—Nita Minnifield
*Attorney, Agent, or Firm*—Hovey, Williams, Timmons & Collins

[57] ABSTRACT

An improved vaccine against infectious bovine keratoconjunctivitis is provided which is derived from an appropriate *Moraxella bovis* strain cultured in a relatively low available iron medium which induces the expression of significant quantities of approximately 78 kDa and 104 kDa outer membrane proteins. The vaccine may be prepared using the entire cell culture or fractions thereof.

10 Claims, 2 Drawing Sheets

METHOD OF CULTURING *M. BOVIS* IN LOW AVAILABLE IRON MEDIA AND ISOLATION OF OUTER MEMBRANE PROTEINS

This application is a continuation of application Ser. No. 08/328,865, filed Oct. 25, 1994, now abandoned.

BACKGROUND OF THE INVENTION

1. Field of the Invention

The present invention is broadly concerned with an improved vaccine for immunizing mammals against keratoconjunctivitis, as well as specialized methods for culturing the etiological microorganism, *Moraxella bovis*. More particularly, the invention pertains to the discovery that *M. bovis*, when cultured in a relatively low available iron content medium, will express substantial quantities of high molecular weight outer membrane proteins, and that such cultures can be employed in the production of highly effective vaccines. Novel mixtures of *M. bovis*-derived outer membrane proteins, and isolated high molecular weight proteins of this type are also disclosed.

2. Description of the Prior Art

Infectious bovine keratoconjunctivitis (IBK), also known as "pinkeye," is a common, specific, infectious, and contagious disease of cattle. The disorder affects cattle on a worldwide scale and is probably the most important bovine ocular disease. It causes inflammation of the conjunctiva, cornea, and eyelids. The disease is characterized by edema, opacities, and vascularization of thee cornea. The result is corneal scarring with associated loss of vision. In severe cases, the cornea may ulcerate and/or rupture, resulting in loss of the eye. While IBK is not a fatal disease, it causes significant economic losses due to the nature of the ocular defects it produces and the populations of susceptible cattle it affects.

IBK was described as early as 1889 as a contagious keratitis affecting dairy cattle. In 1897, the infectious nature of the condition was described. In 1915, an investigator published information that *M. bovis* was the probable cause of IBK.

It has now been established that *M. bovis* is the most common etiologic cause of bovine IBK (Baptista, 1979; Miller et al., 1991; Tamzali et al., 1992). *M. bovis* is a gram-negative, nonmotile, non-fermenting coccobacillus. It can be isolated from the eyes of diseased, convalescent, and normal cattle. Transmission occurs by both direct and indirect contact (e.g., insects) with lacrimal or respiratory secretions and/or exudates. Current vaccines provide limited if any protection (Smith et al., 1990). Virulent and avirulent forms of *M. bovis* have been identified (Pedersen et al., 1972; Leppar et al., 1989; Vandergaast et al., 1989; Ruehl et al., 1993), yet the adaptive events necessary for the organism to colonize the eye and cause disease are not well understood. It is clear however, that the media typically used to grow *M. bovis* in vitro (Riley, 1984; Juni et al., 1986) are by no means similar to the in vivo environment of the bovine eye (Lorian, 1989). In addition, alterations in *M. bovis* associated with in vitro growth occur (McMichael, 1992).

Once attached to the ocular surface, *M. bovis* must overcome host defenses. Bovine tears inhibit the growth of *M. bovis* in vitro (Arora, 1989), although large numbers of organisms can be isolated from the eye of cattle suffering from keratoconjunctivitis and persistent infections are common. As with all bacterial pathogens, *M. bovis* must have the ability to adapt to changing environmental conditions including the ability to acquire sufficient quantities of iron from the host to support protein production and DNA synthesis (Weinberg, 1978). Expression of iron acquisition systems is a significant component of bacterial adaptation to in vivo growth (Bagg et al., 1987; Williams, 1988). Production of siderophores by pathogenic bacteria is regulated by environmental iron concentration and correlated with virulence (Miles et al., 1975; Neilands, 1982; Finkelstein et al., 1983; Griffith, 1987).

A number of potential virulence factors, including pili, leukotoxins, hemolysin, and proteases have been described for *M. bovis* (Tamzali et al., 1992). Of these, pili appear to play a central role in the ability of *M. bovis* to cause keratoconjunctivitis (Ruehl et al., 1988). It has been theorized that pili facilitate attachment to epithelial surfaces and that another pilus type facilitate corneal colonization and help maintain infection (Ruehl et al. 1993). The environmental or intrinsic stimulus which induce shifting of pilus type in *M. bovis* is unknown. In other gram negative bacteria, which like *M. bovis* produce hemolysins and leukotoxins, in vitro growth conditions have a significant effect on production and activity of these toxins (Frey et al., 1988).

There is accordingly a need in the art for an improved vaccine for immunizing cattle and other mammals against IBK.

SUMMARY OF THE INVENTION

The present invention overcomes the problems outlined above, and provides an improved vaccine derived from *M. bovis* cultured under special, relatively low available iron conditions. Such a vaccine may be produced from the entire cell culture, the supernatant thereof, intact cells and/or cellular subunits. Typically, the vaccine is produced by inactivating the cell culture, followed by addition of pharmaceutically acceptable carriers, adjuvants, and/or preservatives.

The first step in vaccine preparation involves growing of an *M. bovis* cell culture by inoculating a colony thereof into a growth medium having a relatively low available iron content, and allowing the colony to grow therein and express outer membrane proteins. The culture medium selected should have a sufficiently low available iron content such that at least about 0.01% by weight of the total expressed outer membrane protein content has a molecular weight of about 104 kDa, as determined by SDS-PAGE electrophoresis and quantified by soft laser densitometry. Preferably, at least about 4% by weight of the total expressed outer membrane content should have this molecular weight.

As an alternate or additional way of establishing whether the growth medium employed has a sufficiently low available iron content, the percent by weight of an approximate 78 kDa outer membrane protein can be determined. In this case, at least about 0.01% by weight of the total expressed outer membrane protein content should have such a protein, and more preferably at least about 25% by weight.

The invention also provides novel mixtures of outer membrane proteins expressed by *M. bovis* and containing the relatively high concentrations of the 78 kDa and/or 104 kDa proteins. Isolated forms of these proteins can also readily be prepared.

DESCRIPTION OF THE PREFERRED EMBODIMENTS

Figure 1:
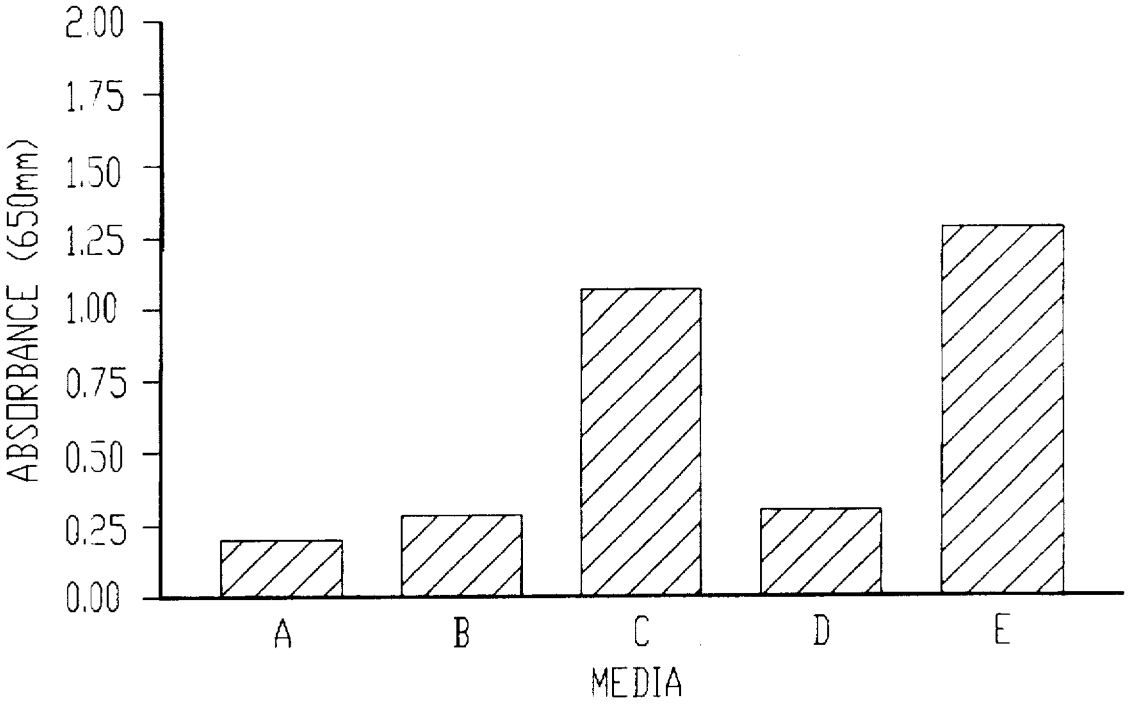
FIG. 1 is a bar graph illustrating the changes in chromeazurol S absolute absorbance ($A_{650nm}$) caused by culture supernatants from *M. bovis* Epp 63 grown in TSB (A), RPMI 1640 (B), RPMI 1640 plus 0.05 mg/ml desferrioxamine (C), RPMI 1640 plus 0.05 mg/ml desferrioxamine and 2 μM $FeSO_4$ (D), and media adapted *M. bovis* grown in RPMI 1640 plus 0.05 mg/ml desferrioxamine (E), wherein all assays were complete after the cultures reached stationary growth, and data presented as the difference between the effect of culture supernatant and uninoculated media and are the mean plus and minus the standard deviation of the mean of triplicate assays.

In carrying out the present invention, colonies of *M. bovis* are inoculated into growth media containing relatively low available iron contents sufficient to induce the expression of substantial quantities of high molecular weight iron-repressible outer membrane proteins. However, the concentration of iron in a given medium is not necessarily a measure of iron availability to *M. bovis*. Thus, a precise definition of the iron content of a given medium which induces iron repressible proteins is not generally applicable. The concentration of iron needed to induce the production of iron-repressible proteins can also vary depending upon the strain of *M. bovis* employed.

Accordingly, whether or not a given culture medium has sufficiently low available iron must be determined functionally, i.e., from the standpoint of the amount and type of outer membrane proteins expressed by the cultured strain of *M. bovis*. In order to ascertain whether the desired functional result is achieved, the outer membrane protein content of a culture medium must be analyzed. Such analyses are conventional and well-established.

In particular, the first step involves isolation of the expressed outer membrane protein fraction. This is accomplished as follows: *M. bovis* is grown overnight at 37° C. in a minimum of 1 liter of liquid media. The culture is allowed to reach stationary growth phase, then the bacteria are harvested and washed three times in a suitable buffer by repeated centrifugation at 10,000 xg for 20 min. at 4° C. Keeping the bacterial suspension cold, it is sonicated repeatedly until the bacterial membranes are fractured and internal cellular components released. Intact bacteria and large cellular debris are pelleted by centrifugation, 5,000 xg for 20 min. at 4° C. The resulting supernatant is centrifuged at 100,000 xg for 2 hours at 4° C. in order to pellet bacterial membrane fragments. This pellet, which should be clear and gel-like, is mixed with an excess of 2% sodium lauryl sarcosinate in sterile saline and incubated for 2 hours at room temperature. The sodium lauryl sarcosinate insoluble fraction is isolated by centrifugation at 100,000 xg for 2 hours at 4° C. The resulting highly enriched pellet of outer-membranes is then resuspended in a minimum amount of distilled water.

Following such isolation, the total protein content for the outer membrane protein preparation is determined. This is done by using the bicinchroninic acid method for the microtiter spectrophotometric determination of protein concentration as described by the manufacturer (Pierce, Rockford, Ill., publication 23225X, incorporated by reference herein). The procedure was originally described by Smith et al., *Measurement of Protein Using Bicinchroninic Acid*, Anal. Biochem. 150:76–85 (1985), also incorporated by reference herein.

The outer membrane protein preparation is then subjected to SDS-polyacrylamide gel electrophoresis (SDS-PAGE) according to the method of Laemmli using a Protean II vertical electrophoresis cell manufactured by Bio-Rad Laboratories of Hercules, Calif. This method is described by Laemmli, *Cleavage of Structural Proteins During the Assembly of the Head of the Bacteriaphace T4*, Nature, 227:680 (1970), incorporated by reference herein.

Following staining, the electrophoretic results are first visually scanned to determine that the requisite protein bands at about 104 and/or 78 kDa are present. If no such bands are visible, then it is established that the growth medium originally used contained excess available iron, and the dictates of the present invention were accordingly not met.

In the final analysis, the results of the electrophoresis are scanned using conventional soft laser densitometry techniques in order to determine the approximate amount by weight of the characteristic high molecular weight outer membrane proteins having approximate molecular weights of 104 kDa and/or 78 kDa. Polyacrylamide electrophoresis gels of the outer membrane preparations are scanned into ImageQuant v3.0 files on a Molecular Dynamics Computing Densitometer, Model 300A (Molecular Dynamics, Inc., Sunnyvale, Calif.). Using the method as described in Chapter 7 of the ImageQuant v3.0 user's Guide (Molecular Dynamics, Inc., Sunnyvale, Calif.), the relative band migration and percentage of total protein represented by each individual protein band was determined for each lane by area integration as described in Chapter 9. Peak recognition parameters were adjusted for optimal sensitivity following recommendations in Section 9.6. Data was transferred to Microsoft EXCEL v4.0 as described in Chapter 16. Molecular mass of individual protein bands were estimated using a graph of molecular weight as determined by the migration of molecular mass protein standards. The aforementioned User's Guide is incorporated by reference herein.

When reference is made herein to the determination of the percent by weight of a total outer membrane protein content which has a molecular weight of about 104 and/or 78 kDa by gel electrophoresis and soft laser densitometry, use of the above-described procedures, explained in more detail hereinafter, is intended and assumed.

The following examples describe the growth of *M. bovis* in restricted iron media in order to induce the expression of high molecular weight iron-repressible outer membrane proteins. Techniques believed to be useful in the production and use of vaccines are also given. It is to be understood that these examples are provided by way of illustration only, and nothing therein should be taken as a limitation upon the overall scope of the invention.

EXAMPLE 1

The purpose of this example was to evaluate the effects of the expression of outer membrane proteins and changes in the iron affinity of culture supernatants when growing *M. bovis* in iron restricted conditions. A chemically defined medium was chosen in order to provide in vitro growth conditions which could be controlled precisely. The iron chelator desferrioxamine B mesylate was used as a means of sequestering iron in the growth media.

MATERIALS AND METHODS

Bacteria

*Moraxella bovis* strain Epp 63 was stored at −70° C. in 0.1 ml aliquots of double strength sterile skim milk. For each experiment, frozen bacteria were first grown on bovine blood agar and individual colonies inoculated into liquid culture medium. Sterility checks, reisolations, and colony forming unit determinations were performed on blood agar.

Media

Tryptic soy broth (DIFCO Laboratories, Detroit, Mich.) and RPMI medium 1640 with L-glutamine (Gibco Laboratories, Grand Island, N.Y.) were purchased. The media was reconstituted with distilled deionized water following the manufacturer's instructions. Sodium bicarbonate (2 g/l) was added to the RPMI, pH adjusted to 7.2, and filter sterilized using self-contained disposable 2 μm cellulose acetate filter units (Costar Corp., Cambridge, Mass.). Bacteria were grown either directly in the filtrate receptacle or in sterile plastic disposable 50 ml centrifuge tubes (Corning Corp., Corning, N.Y.).

Desferrioxamine mesylate (Ciba Pharmaceutical Co, Summit, N.J.) was added to RPMI 1640 in order to further reduce the readily available iron in the medium. To counter the iron sequestration associated with desferrioxamine, various concentrations of $FeSO_4 \cdot H_2O$ were added to the prepared media. Total iron concentration of the various media was determined using Ferrochem II Iron Analyzer (ESA, Inc., Bedford, Mass.).

Growth Rate

At regular intervals following inoculation, growth rates were determined by changes in optical density (650 nm) of 250 μl of media in flat-bottom microtiter plates using a Vmax Kinetic Microplate Reader equipped with SOFTmax software (Molecular Devices Corp., Palo Alto, Calif.).

Chromeazurol S assay

Culture supernatants were collected by centrifugation (20 min×20,000 g) when the cfu of each media was approximately equal (early stationary phase). The iron binding affinity of each supernatant was estimated by chromeazurol S (CAS) assay essentially as described (Schwyn et al., 1987). The assay was conducted in triplicate using 96 well microtiter plates (Pro-bind, Falcon, Lincoln Park, N.J.) and the optical density measured (650 nm). The CAS assay results were normalized with RPMI 1640 containing 0.05 mg/ml desferrioxamine which served as a positive control. Fresh media was used as a negative control. A solid CAS assay system was developed by addition of the CAS reagent to RPMI 1640, and agar (DIFCO) added to produce CAS-RPMI 1640 agar plates. The ability to acquire iron from the CAS reagent was demonstrated by the agar near bacterial colonies changing color from a greenish-purple to yellow.

Outer Membrane Proteins

Outer membrane proteins (OMP) were isolated from approximately the same number (wet weight) of *M. bovis* followed by N-lauroyl sarcosinate selective solubilization of inner membranes as described (Squire et al., 1984). The total protein content for each OMP preparation was determined (BCA Protein Assay, Pierce, Rockford, Ill.) and the preparations analyzed by 7.5% sodium dodecyl sulfatepolyacrylamide gel electrophoresis (SDS-PAGE) and stained with either coomassie brilliant blue (FastStain, Zoion Research Inc., Allston, Mass.) or silver (Bio-Rad Silver Stain Kit, Bio-Rad Laboratories, Richmond, Calif.). Individual lanes were loaded with approximately the same total amount of protein.

RESULTS

To begin the process of evaluating the effects of iron limitation on the expression of outer membrane proteins and iron acquisition system(s) of *M. bovis*, the organism was grown in chemically defined media, RPMI 1640. The total iron in RPMI 1640 is 0.03 μg/ml (0.51 μmol/l). The addition of desferrioxamine did not measurably increase total iron content of the media. Addition of approximately 10 μg/ml $FeSO_4 \cdot 7H_2O$ to RPMI increased the total measurable iron concentration to 170.00 μmol/l. While more variable, the average total iron concentration of tryptic soy broth averaged 0.87 μg/ml (14.79 μmol/l).

Growth rate was used as an indication of iron limited conditions. The growth rate of *M. bovis* in RPMI was similar to the rate of growth in tryptic soy broth. Addition of desferrioxamine at concentrations greater than 0.05 mg/ml prevented growth. Under these conditions, the organism did not die immediately but gradually declined over time. At a desferrioxamine concentration of 0.05 mg/ml growth occurred only after an extended lag phase in comparison to growth in RPMI 1640 without desferrioxamine. Following passage of *M. bovis* in RPMI 1640 desferrioxamine medium (0.05 mg/ml), the growth rate was similar to that in RPMI 1640 without desferrioxamine. The media adapted strains of *M. bovis* were able to grow-in the presence of higher concentrations of desferrioxamine (greater than 0.05 mg/ml) than was originally possible. To counter the iron sequestration associated with the addition of desferrioxamine to RPMI 1640, $FeSO_4.7H_2O$ was added at various concentrations. At 2 μM $FeSO_4$, growth of non-adapted *M. bovis* strains approximated the growth rate in RPMI 1640 without desferrioxamine.

Media dependent changes in the ability of *M. bovis* culture supernatants as well as bacteria cultured on agar to remove iron from chromeazurol S were evaluated as a means of detecting the production of high affinity iron ligand(s), (putative siderophore). Removal of iron for the chromeazurol S—iron complex causes a color shift which is measured spectrophotometrically. The CAS assay results from different culture supernatants (FIG. 1) demonstrate presence of iron-binding compound(s) with an affinity greater than chromeazurol S. Supernatants of cultures containing *M. bovis* adapted to growth in RPMI 1640—desferrioxamine media had the greatest increase in ability to remove iron from chromeazurol S. Growth of *M. bovis* on RPMI 1640—CAS agar caused the agar to turn yellow in a well-defined ring around individual colonies. This reaction was also most pronounced after *M. bovis* had been adapted to growth in RPMI 1640—desferrioxamine.

The SDS-PAGE gel evaluations (FIGS. 2 and 3) of the OMPs from *M. bovis* grown in different media demonstrated the presence of relatively high molecular weight proteins under relatively low iron media conditions. For example, in FIG. 3, lane A, the presence of substantial amounts of approximately 104 kDa and 78 kDa outer membrane proteins is manifest, as compared with lanes B and C having substantially higher available iron media. Similarly, in FIG. 2, lanes A–C, the approximately 104 kDa and 78 kDa outer membrane proteins are clearly present, as compared with lanes E and F. It will also be observed that the relatively low available iron media lessened the amounts of the lower molecular weight outer membrane proteins of approximately 34 and 45 kDa.

The expression of bacterial virulence factors associated with differing growth conditions is well established. One of the best studied is the effect of growth in iron-restricted conditions. Bacteria pathogens have developed elaborate systems to acquire iron from their hosts (Neilands, 1982; Griffith, 1987). However, the iron acquisition system(s) of *M. bovis* and the effect of iron restriction on expression of virulence factors have not been investigated previously.

RPMI medium 1640 was selected as a medium to grow *M. bovis* because it is chemically defined, has been shown to enhance the production of cytotoxins in other bacteria, and has a relatively low iron concentration in comparison to media typically used to grow *M. bovis*. The variability in the iron concentration of less defined media (e.g. TSB, brain heart infusion, protease peptone) complicated their use in producing media with a consistent iron concentration. In contrast to several other species of bacteria, *M. bovis* grew well in unsupplemented RPMI 1640. Given the low iron concentration in unsupplemented RPMI 1640, a high growth rate suggests *M. bovis* has one or more high affinity iron acquisition systems.

Desferrioxamine was used to further reduce the available iron in the media. Desferrioxamine is a siderophore isolated from *Streptomyces pilosus*. It is very selective for iron, is stable, and will remove iron from transferrin, hemosiderin, and ferritin. It was selected for use in these experiments because it is better than synthetic iron chelating agents because of superior specificity to Fe+3 and the lack of toxicity.

At high concentrations of desferrioxamine (>0.05 μg/ml), growth of *M. bovis* was inhibited while at lower concentrations growth occurred but a reduced rate. This plus the ability of *M. bovis* to adapt to grow in media containing desferrioxamine indicates that *M. bovis* produces an iron binding ligand with an affinity approximately equal to that of desferrioxamine and that its expression can be increased.

In the RPMI 1640 culture system, an equilibrium between soluble iron, iron bound to desferrioxamine, and iron bound to the ligand(s) produced by *M. bovis* was established. In the absence of desferrioxamine, iron was not a growth limiting factor. At high concentrations of desferrioxamine, the iron equilibrium was shifted towards desferrioxamine and sufficient iron to support growth of *M. bovis* was not available. The small amount of desferrioxamine (0.05 mg/ml) necessary to inhibit *M. bovis* growth is consistent with the low iron content of RPMI 1640. Growth was notably increased when the $FeSO_4$ was added in concentrations adequate to saturate desferrioxamine. At low concentrations of desferrioxamine, growth rate was reduced (long lag phase) until *M. bovis* produced sufficient amounts of iron binding ligand to overcome the iron sequestration effect of desferrioxamine. Additional proof was provided when *M. bovis* was adapted to growth in RPMI containing desferrioxamine, i.e., growth was also possible at desferrioxamine concentrations that were once inhibitory (<0.05 mg/ml).

Failure of bioassays to detect siderophores is rarely conclusive because the assay depends on the organism being examined to produce a siderophore capable of supplying iron to the auxotrophic test strain. The inconclusive nature of these bioassays prompted the use of the CAS assay as a screening test. The CAS siderophore assay of Schywn et al. (1987) is universal in its ability to detect any form of iron-binding ligand. The CAS assay is particularly well suited for initial investigations of siderophore activity as removal of iron from chromeazurol S can be spectrophotometrically measured thus providing an estimate of the iron binding affinity of the media. The iron binding affinity of chromeazurol S is sufficiently great so that only ligands with iron binding affinities similar to that of bacterial siderophores are capable of removing iron for the chromeazurol S—iron complex.

In the CAS assay, a dynamic iron equilibrium is established between soluble iron, chromeazurol S, and iron binding ligand(s) (desferrioxamine or produced by *M. bovis*). The color shift associated with growth in RPMI 1640 on CAS-RPMI agar plates as well as the ability of culture supernatants to cause a color shift in the CAS reagent provides evidence that *M. bovis* produces a iron binding ligand with an affinity greater than chromeazurol S. Addition of $FeSO_4$ effectively iron saturates the media system as demonstrated by minimal change in absorbance in the CAS assay.

When *M. bovis* was adapted to grow in RPMI 1640 plus low concentrations of desferrioxamine (0.05 mg/ml), the change in absorbance of chromeazurol S was greater than the sum of the change caused by desferrioxamine alone (uninoculated media) plus the culture supernatant from *M. bovis* grown in RPMI 1640 without desferrioxamine (FIG. 1). This difference might be related to the increased growth rate following adaptation except that careful steps were taken to account for differences in increased growth rate between adapted and nonadapted strains. This finding supports the growth data that the production of the iron binding ligand(s) by *M. bovis* increases as iron availability decreases. The iron ligand(s) produced by *M. bovis* can compete with desferrioxamine for iron as well as readily acquire iron from chromeazurol S. Given that the iron binding affinity of these compounds are greater than transferrin and lactoferrin, it seems likely that *M. bovis* could acquire iron from these host proteins. However, no direct evidence of this phenomenon is available.

Figure 2:
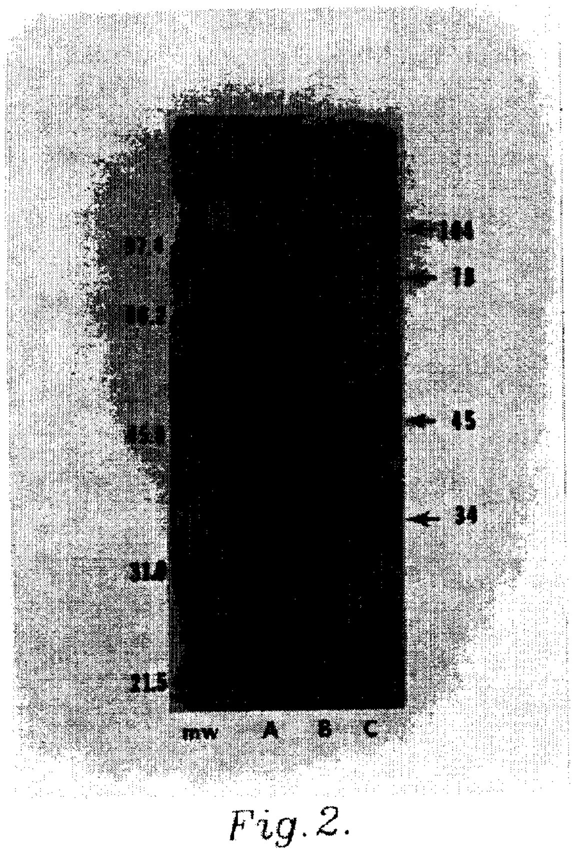
FIG. 2 is a photograph depicting the results of an SDS—(10%) polyacrylamide gel electrophoresis (stained with coomassie brilliant blue) demonstrating the importance of media available iron content in the expression of the *M. bovis* outer membrane proteins of the present invention, wherein lane MW equals molecular weight markers in kDa; lane A equals growth in RPMI 1640 (iron concentration=<0.03 mg/ml); lane B equals growth in RPMI 1640 supplemented with iron sulfate (iron concentration=5.3 mg/ml); and lane C equals growth in tryptic soy broth (iron concentration=8.7 mg/ml)
Figure 3:
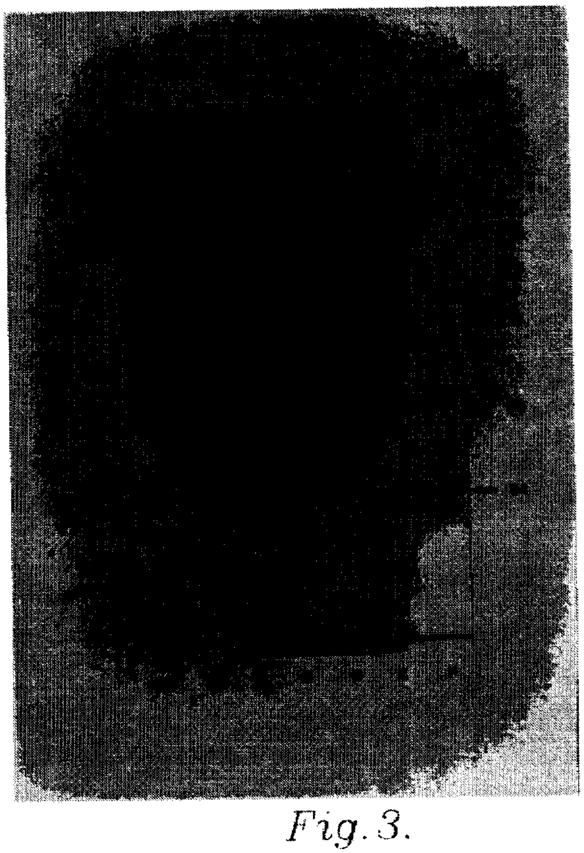
FIG. 3 is a photograph depicting the results of an SDS—(10%) polyacrylamide gel electrophoresis (stained with coomassie brilliant blue) demonstrating the importance of media available iron content in the expression of the *M. bovis* outer membrane proteins of the present invention, wherein lane MW equals molecular weight markers in kDa; lane A equals growth in RPMI 1640 supplemented with 0.05 mg/ml desferrioxamine mesylate (iron concentration=<0.03 mg/ml); lanes B and C are different preparations following growth in RPMI 1640 (iron concentration=<0.03 mg/ml); lane D equals growth in RPMI 1640 supplemented with 0.05 mg/ml desferrioxamine mesylate and iron sulfate (iron concentration=1.2 mg/ml); lane E equals growth in RPMI 1640 supplemented with iron sulfate (iron concentration=5.3 mg/ml); and lane F equals growth in tryptic soy broth (iron concentration=8.7 mg/ml).

To evaluate the effect of iron starvation on the OMPs of *M. bovis*, the Epp strain was grown in TSB, RPMI 1640, RPMI 1640—desferrioxamine, and RPMI 1640—desferrioxamine—$FeSO_4$ media. Desferrioxamine induced the production of previously unrecognized, high molecular weight outer membrane proteins which were repressed by the addition of $FeSO_4$ (FIGS. 2 and 3). While these proteins are clearly iron repressible, it should be noted that their role (if any) in iron acquisition is uncertain. The proteins isolated from *M. bovis* in this example are different from those described previously (Ostle et al., 1985). This may be related to the strain of *M. bovis* used although strain dependent differences were not detected in the original study. It is believed that the difference is related to the media used to grow *M. bovis*.

Taken together, the growth data and CAS assay results provide evidence that *M. bovis* produces one or more siderophores. In addition, under conditions of iron starvation *M. bovis* produces a number of previously unrecognized OMPs. The proteins associated with iron-acquisition systems are conserved within a given bacterial species and are known to play a role in protective immunity (Chart et al., 1985; Bolin et al., 1987).

EXAMPLE 2

In this example, the preparation and use of an *M. bovis* vaccine is described.

In preparing such a vaccine, an *M. bovis* strain isolated from clinical cases or obtained from available sources is used. The Epp 63 strain described above is suitable. The bacteria is grown on or in common bacterial culture media, such as RPMI-1640 medium, so long as the actual or available iron content of the medium is low or is necessarily reduced to the point that iron-repressible proteins are expressed. If use is made of media having an inherently high available iron content, the iron is removed by exposure to iron chelating agents and/or chemicals, such as desferrioxamine mesylate, Chelx-100, or 2,2'-dipyridyl.

Once *M. bovis* seed stock is inoculated into a medium containing an available iron concentration sufficiently low to induce the expression of iron-repressible proteins, the culture is maintained so that it has a high oxygen content, neutral or slightly alkaline pH, and a constant temperature of from about 30°–35° C. The culture is incubated until cell density is at least about 2.0 absorbance units at 590 nm. A portion of the cells are isolated and examined for expression of the minimum amounts required of the 104 kDa and/or the 78 kDa iron-repressible outer membrane proteins; such analyses are conducted as described previously.

After determining cell density and purity, the culture is cooled and inactivated by the addition of known agents such as formaldehyde, β-propiolactone or glutaraldehyde.

Adjuvants and/or preservatives may optionally be added to the inactivated culture. Alternately, intact cells or cellular subunits may be removed from the culture medium, before or after inactivation, and the isolated cells, subunits, or the supernatant derived from the culture, can be used as a vaccine. Combinations of these materials can also be used.

The vaccine produced as described herein is administered by injection to calves, and the injection site(s), dose, and frequency would be determined based upon the potency of the vaccine and the characteristics of the animals involved.

REFERENCES

The following references are pertinent and/or referred to herein.

Arora, A. K., 1989. Studies on *Moraxella bovis* isolated from cattle affected with or convalescing from infectious bovine keratoconjunctivitis. Veterinarski-Arhiv., 59:17–23.

Bagg, A., Neilands, J. B., 1987. Molecular mechanism of regulation of siderophore-mediated iron assimilation. Microbiol. Rev., 51:509–518.

Baptista, P. J. H. P., 1979. Infectious bovine keratoconjunctivitis, a review. Br. Vet. J., 135:225–242.

Bolin, C. A. Jensen, A. E., 1987. Passive immunization with antibodies against the iron-regulated outer membrane proteins protects turkeys from *Escherichia coli* septicemia. Infect. Immun. 55:1239–1242.

Chart, H., Griffiths, E., 1985. Antigenic and molecular homology of the ferric enterobactin receptor protein of *Escherichia coli*. J. Gen. Microbiol. 131:1503–1509.

Frey, J., Nicolet, J., 1988. Regulation of hemolysin expression in *Actinobacillus pleuropneumoniae* serotype 1 by $Ca^{2+}$. Infect. Immun. 56:2570–2575.

Finkelstein, R. A., Sciortino, C. V., McIntosh M. A., 1983. Role of iron in microbe-host interactions. Rev. Infect. Dis., 5(Suppl.):S759–S777.

Griffith, E., 1987. Iron and Infection. John Wiley & Sons Pub., N.Y., pp. 171–210.

Juni, E., Heym, G. A., 1986. Defined medium for *Moraxella bovis*. App. Environ. Micro., 52:966–968.

Leppar, A. W. D., Power, B. E., 1989. Infectivity and virulence of Australian strains of *Moraxella bovis* for the murine and bovine eye in relation to pilus serogroup sub-unit size and degree of piliation. Aust. Vet. J., 65:305–309.

Lorian, A., 1989. In vitro simulation of in vivo conditions: physical state of the culture medium. J. Clin. Microbiol., 27:2403–2406.

McMichael, J. C., 1992. Bacterial differentiation of *Moraxella bovis* colonies growing at the interface of the agar medium with the petri dish. J. Gen. Microbiol., 138:2687–2695.

Miles, A. A., Khimji P. L., 1975. Enterobacterial chelators of iron: their occurrence, detection and relation to pathogenicity. J. Med. Microbiol., 8:477–490.

Miller, T. R. and Gelatt, K. N., 1991. Food Animal Ophthalmology, In: K. N. Gelatt (Ed.), Veterinary Ophthalmology, 2nd ed., Lea and Feibiger, Philadelphia, pp. 619–624.

Neilands, J. B., 1982. Microbial envelope proteins related to iron. Ann. Rev. Microbiol., 36:285–309.

Ostle, A. G., Rosenbusch, R. F., 1985. Outer membrane protein antigens of *Moraxella bovis*. Am. J. Vet. Res., 47:1419–1421.

Pedersen, K. B., Froholm, L. O., Bovre, K., 1972. Fimbriation and colony type of *Moraxella bovis* in relation to conjunctival colonization and envelopment of keratoconjunctivitis in cattle. Acta. Pathol. Microbiol. Scand., 80:911–918.

Riley, W. T., 1984. Growth requirements for *Moraxella bovis*. Vet. Micro., 9:593–598.

Ruehl, W. W., Marrs, C. F., Fernandez R., 1988. Purification, characterization, and pathogenicity of *Moraxel la bovis* pili. J. Exp. Med., 168:983–1002.

Ruehl, W. W., Marrs, C. F., George, L., Banks, S. J. M., Schoolnik, G. K., 1993. Infection rates, disease frequency, pilin gene rearrangement, and pilin expression in calves inoculated with *Moraxella bovis* pilin-specific isogenic variants. Am. J. Vet. Res., 54:248–253.

Schwyn, B., Neilands, J. B., 1987. Universal chemical assay for the detection and determination of siderophores. Anal. Biochem., 160:47–56.

Smith, P. G., Blankenship T., Hoover T. R., Powe, T., Wright, J. C., 1990. Effectiveness of two commercial infectious bovine keratoconjunctivitis vaccines. Am. J. Vet. Res., 51:1147–1150.

Squire, P. G., Smiley D. W., Croskell, R. B., 1984. Identification and extraction of *Pasteurella haemolytica* membrane proteins. Infect. Immun., 45:667–673.

Tamzali, Y., Marmignon, J., 1992. Review of infectious bovine keratoconjunctivitis. Maghreb-Veterinaire, 7:8–16.

Vandergaast, N., Rosenbusch, R. F., 1989. Infectious bovine keratoconjunctivitis epizootic associated with area-wide emergence of a new *Moraxella bovis* pilus type. Am. J. Vet. Res., 50:1437–1441.

Weinberg, E. D., 1978. Iron and infection. Microbiol. Rev., 42:45–66.

Williams, P., 1988. Role of the cell envelope in bacterial adaptation to growth in vivo in infections. Biochimie., 70:987–1011.

We claim:

1. A method of producing a *M bovis* cell culture comprising the steps of inoculating a colony of *M bovis* in a growth medium and causing said colony to grow therein and express outer membrane proteins, said medium having a low available iron content resulting in at least about 0.01% by weight of the total expressed outer membrane protein content having a molecular weight of about 104 kDa, as determined by sodium dodecyl sulfate polyacrylamide gel electrophoresis and quantified by soft laser densitometry.

2. The method of claim 1, wherein at least about 4% by weight of said total expressed outer membrane protein content has a molecular weight of about 104 kDa.

3. The method of claim 1, wherein at least about 0.01% by weight of said total expressed outer membrane protein content has a molecular weight of about 78 kDa.

4. The method of claim 3, wherein at least about 25% by weight of said total expressed outer membrane protein content has a molecular weight of about 78 kDa.

5. A mixture of isolated outer membrane proteins derived from *M bovis*, said mixture including an outer membrane protein having a molecular weight of about 104 kDa, as determined by sodium dodecyl sulfate polyacrylamide gel electrophoresis.

6. The mixture of claim 5, wherein at least about 4% by weight of said mixture is said protein having said molecular weight of about 104 kDa.

7. The mixture of claim 5, wherein at least about 0.01% by weight of said mixture is an outer membrane protein having a molecular weight of about 78 kDa.

8. The mixture of claim 7, wherein at least about 25% by weight of said mixture is said protein having said molecular weight of about 78 kDa.

9. An isolated outer membrane protein derived from *M. bovis* and having a molecular weight of about 104 kDa.

10. The mixture of outer membrane proteins produced by the method of claim 1.

* * * * *